(12) United States Patent
McCarthy et al.

(10) Patent No.: US 9,217,127 B2
(45) Date of Patent: *Dec. 22, 2015

(54) ORGANIC CLEANING COMPOSITION

(71) Applicant: Greenology Products, Inc., Raleigh, NC (US)

(72) Inventors: Adam McCarthy, Raleigh, NC (US); David Andrew Gordon, Lafayette, LA (US)

(73) Assignee: GREENOLOGY PRODUCTS, INC., Raleigh, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 14/486,644

(22) Filed: Sep. 15, 2014

(65) Prior Publication Data

US 2015/0005215 A1  Jan. 1, 2015

Related U.S. Application Data

(63) Continuation-in-part of application No. 14/046,692, filed on Oct. 4, 2013, now Pat. No. 8,835,370, which is a continuation of application No. 13/959,311, filed on Aug. 5, 2013, now abandoned.

(51) Int. Cl.

| | |
|---|---|
| *C11D 9/38* | (2006.01) |
| *A61Q 5/02* | (2006.01) |
| *A61Q 19/10* | (2006.01) |
| *A61K 8/92* | (2006.01) |
| *A61K 8/19* | (2006.01) |
| *A61K 8/97* | (2006.01) |
| *C11D 9/12* | (2006.01) |
| *C11D 9/26* | (2006.01) |

(52) U.S. Cl.
CPC ... *C11D 9/38* (2013.01); *A61K 8/19* (2013.01); *A61K 8/922* (2013.01); *A61K 8/97* (2013.01); *A61Q 5/02* (2013.01); *A61Q 19/10* (2013.01); *C11D 9/12* (2013.01); *C11D 9/262* (2013.01)

(58) Field of Classification Search
CPC ........................................................ A01N 65/08
See application file for complete search history.

(56) References Cited

U.S. PATENT DOCUMENTS

| | | | |
|---|---|---|---|
| 2013/0295204 A1* | 11/2013 | Silberstein | 424/725 |
| 2014/0031305 A1* | 1/2014 | Terrisse et al. | 514/25 |

FOREIGN PATENT DOCUMENTS

| | | |
|---|---|---|
| CN | 102517177 A | 6/2012 |
| CN | 102965217 A | 3/2013 |
| CN | 103122287 A | 5/2013 |

OTHER PUBLICATIONS

Non-Final Office Action dated May 21, 2015 from related U.S. Appl. No. 14/615,288.
Non-Final Office Action dated Dec. 4, 2013 from related U.S. Appl. No. 14/046,692.
Final Office Action dated Apr. 28, 2014 from related U.S. Appl. No. 14/046,692.

* cited by examiner

*Primary Examiner* — Necholus Ogden, Jr.
(74) *Attorney, Agent, or Firm* — Ward and Smith, P.A.; Jeffrey W. Childers

(57) ABSTRACT

Organic cleaner/detergent compositions, formulations and solutions, and methods of cleaning using such compositions, formulations and solutions and manufacturing such compositions, formulations and solutions are disclosed. More particularly, compositions; formulations and solutions used for the cleaning and/or cleansing of a variety of industrial, domestic and/or communal hard surfaces, fiber/soft surfaces, including all natural, organic, synthetic and blended fibers, and organic surfaces, including, but not limited to, human skin and hair and animal skin and hair are disclosed. Such compositions, formulations and solutions are useful as laundry detergents, automatic dishwasher detergents, hard surface cleaners, hand soaps, human shampoos, and animal shampoos.

20 Claims, No Drawings

ORGANIC CLEANING COMPOSITION

REFERENCE TO RELATED APPLICATIONS

This application is a continuation-in-part of U.S. patent application Ser. No. 14/046,692, filed Oct. 4, 2013, now U.S. Pat. No. 8,835,370, issued Sep. 16, 2014, which is a continuation of U.S. patent application Ser. No. 13/959,311, filed Aug. 5, 2013, now abandoned, the content of which is herein incorporated by reference in its entirety.

BACKGROUND

Most commercial cleaning/detergent formulations are designed to efficiently clean either industrial, domestic and/or communal hard surfaces, soft surfaces, including all natural, organic, synthetic and blended fibers, or organic surfaces including, but not limited to, human skin and hair and animal skin and hair, but not all three. Compositions, formulations and solutions known in the art generally comprise a solution of surfactants having various ionic charges, in particular surfactants that are non-ionic, anionic, cationic, or amphoteric in nature, acids, caustics, solvents, penetrating agents, oils, and/or alcohols. Many of these formulations are harsh, however, and are not naturally occurring.

Other detergent/cleaner formulations known in the art include linear alkylbenzene sulfonates (LASs), e.g., sodium dodecylbenzenesulfonate, 2-butoxyethanol, chlorine bleach (e.g., sodium hypochlorite (NaOCl)), and other synthetic or manmade chemicals, such as glycols and non-natural surfactants and ammonia, many of which are toxic and damaging to the environment. In cases of intensive prolonged exposure, such chemicals can be toxic to those using the compositions for cleaning. Over time, the toxic effects of such compositions have become more widely known, and it has become desirable to attempt to avoid exposure to such toxic materials.

SUMMARY

The presently disclosed subject matter provides a cleaning/detergent composition, formulation and/or solution that primarily comprises naturally occurring ingredients, provides effective cleaning/detergent action on a variety of surfaces, and is generally safe(r) to use and is less toxic to the user and the environment than existing cleaning/detergent compositions.

In some aspects, the presently disclosed subject matter provides an organic cleaning mixture, comprising one or more soapberry extracts, one or more saponified oils, and optionally one or more of sodium carbonate (also referred to herein as washing soda), sodium hydroxide, and potassium hydroxide, mixed in varying ratios in a solvent in an amount sufficient for the mixture to exhibit commercially acceptable cleaning properties.

In particular aspects, the mixture comprises up to about ninety five percent (95%) by weight soapberry extract, up to about thirty three percent (33%) by weight saponified oil, and up to about three percent (3%) by weight sodium carbonate, not including water.

In yet other aspects, the mixture comprises up to about eighty two percent (82.0%) by weight soapberry extract, twelve percent (12.0%) by weight saponified oil, and one point five percent (1.5%) by weight sodium carbonate, not including water.

In other aspects, the mixture comprises from about five percent (5%) to about ninety five percent (95%) by weight soapberry extract, from about 0.1% to about one hundred percent (100%) by weight saponified oil, and optionally from about 0.5% to about thirty percent (30%) by weight of one or more of sodium carbonate, sodium hydroxide, and potassium hydroxide, not including water.

In particular aspects, the mixture comprises from about twenty percent (20%) to about eighty-five percent (85%) by weight soapberry extract, from about 0.1% to about eighty percent (80%) by weight saponified oil, and optionally from about 0.5% to about thirty percent (30%) by weight of one or more of sodium carbonate, sodium hydroxide, and potassium hydroxide, not including water.

In yet more particular aspects, the mixture comprises from about sixty-five percent (65%) to about eighty-five percent (85%) by weight soapberry extract, from about ten percent (10%) to about twenty-five percent (25%) by weight saponified oil, from about 1% to about 15% of a thickener, and optionally from about 0.5% to about three percent (3%) by weight of one or more of sodium carbonate, sodium hydroxide, and potassium hydroxide, not including water.

In even yet more particular aspects, the mixture further comprises one or more components selected from the group consisting of hydrogen peroxide, ethyl palmate, sodium hydroxide, calcium chloride, one or more enzymes, silica, and one or more fragrances.

In further aspects, the mixture comprises from about 0.0% to about five percent (5%) by weight soapberry extract, from about 90 percent (90%) to about one hundred percent (100%) by weight saponified oil, from about 1% to about 15% by weight of a thickener, and optionally from about 0.5% to about three percent (3%) by weight of one or more of sodium carbonate, sodium hydroxide, and potassium hydroxide, not including water.

In yet further aspects, the mixture comprises from about twenty percent (15%) to about twenty-five percent (25%) by weight soapberry extract, from about seventy percent (70%) to about eighty percent (80%) by weight saponified oil, from about 1% to about 15% of a thickener, and optionally from about 0.5% to about thirty percent (30%) by weight of one or more of sodium carbonate, sodium hydroxide, and potassium hydroxide, not including water.

Such materials are mixed in a solution, for example, in some aspects, with water, for use as a cleaning/detergent composition.

Certain aspects of the presently disclosed subject matter having been stated hereinabove, which are addressed in whole or in part by the presently disclosed subject matter, other aspects will become evident as the description proceeds when taken in connection with the accompanying Examples as best described herein below.

DETAILED DESCRIPTION

The presently disclosed subject matter now will be described more fully hereinafter with reference to the accompanying Examples, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Examples. Therefore, it is to be understood that the presently disclosed subject matter is not to be limited to the specific embodiments disclosed and that modifications and other embodiments are intended to be included within the scope of the appended claims.

I. Organic Cleaning Composition

In some embodiments, the presently disclosed subject matter provides an organic cleaning/detergent composition, formulation and/or solution. In particular embodiments, the presently disclosed solutions comprise a carrier, such as blend water, comprising effective amounts of a soapberry extract in combination with one or more saponified oils, glycerin, optionally one or more of sodium carbonate, sodium hydroxide, and potassium hydroxide for pH adjustment (if required) or as a residual reagent from the saponification process; and a natural viscosifier or thickening agent. Such a solution can be used as a cleaning agent/detergent, which exhibits commercially acceptable cleaning properties.

As used herein, the term "commercially acceptable cleaning properties" refers generally to the degree of cleanliness, extent of effort, or both that a typical consumer would expect to achieve or expend when using a cleaning product or cleaning system to address a typical soiling condition on a typical substrate or surface. This degree of cleanliness may, depending on the particular cleaning product and particular substrate, correspond to a general absence of visible soiling, or to some lesser degree of cleanliness. For example, a cleaner for a hard surface would be expected by a typical consumer to achieve an absence of visible soiling when used on a moderately soiled, but relatively new hard surface, but would not be expected to achieve an absence of visible soiling when used on an old hard surface that already bears permanent stains or discoloration. Cleanliness may be evaluated in a variety of ways depending on the particular cleaning product being used (e.g., laundry detergent, hard surface cleaner, or the like) and the particular hard, soft, or organic surface being cleaned, and normally may be determined using generally agreed industry standard tests or localized variations of such tests. In the absence of such agreed industry standard tests, cleanliness may be evaluated using the test or tests already employed by a manufacturer or seller to evaluate the cleaning performance of its cleaning products sold in association with its brand.

Further, although the term "blend water" is used in connection with the term "solution," at least one of the components of the presently disclosed composition can, in some embodiments, be only "miscible" in water and accordingly does not go into solution. Thus, the term "solution" is intended to encompass all such terms as "composition," "formulation," "mixtures," "emulsions," and "solutions" and such terms are used interchangeably herein.

Soapberries, also referred to as "soapnuts" are the fruit of shrubs or small trees belonging to the genus *Sapindus*, which includes a number of species including, but not limited to, *Sapindus delavay, Sapindus detergens, Sapindus emarginatus, Sapindus laurifolius, Sapindus marginatus, Sapindus mukorossi, Sapindus oahuensis, Sapindus rarak, Sapindus saponaria, Sapindus tomentosus, Sapindus trifoliatus*, and *Sapindus vitiensis*.

For example, fruit from the *Sapindus mukurossi* tree also is known as washnut, tiha, reetha, aritha, dodan, and doadni, as well as soapberry or soapnut. The *Sapindus mukurossi* tree is a deciduous tree widely grown in upper reaches of Indo Gangetic plains, Shivaliks and sub Himalayan tracts at altitudes from 200 m to 1500 m. *Sapindus mukurossi* fruit extract has cleansing, anti-bacterial, and anti-fungal properties, among others, and it provides a less irritating alternative to non-natural chemical formulations.

In some embodiments, the bark of bush or tree from the genus *Sapindus* can be used, and is referred to herein as "soapbark." In representative, non-limiting embodiments, the soapbark can be obtained from an *Quillaja saponaria*, or so-called "soap bark," tree. Soap bark can impart detergency properties, as well as function as a foaming agent.

These properties have been attributed to the saponin found in soapberries and soapbark. Saponins are natural surfactants and have a diverse range of properties, including foaming, cleaning and emulsifying, pharmacological and medicinal, and haemolytic properties, as well as antimicrobial, insecticidal, spermicidal and molluscicidal activities. Saponins are amphipathic glycosides comprising one or more hydrophilic glycoside moieties combined with a lipophilic triterpene derivative. Generally, saponins are the glycosides of 27 carbon steroids or 30 carbon triterpenes.

Soapberries have been used for washing for thousands of years by native peoples and have been included, for example, in natural laundry detergents.

In some embodiments, the soapberry extract is provided in an amount ranging from about sixty five percent (65%) to about ninety five percent (95%), including 65%, 70%, 75%, 80%, 85%, 90%, and 95%, and any integer percentage and fraction thereof from 65% to 95%, depending on product function. In other embodiments, the soapberry extract is provided in an amount ranging from about five percent (5%) to about ninety five percent (95%), including 5%, 10%, 15%, 20%, 25%, 30%, 35%, 40%, 45%, 50%, 55%, 60%, 65%, 70%, 75%, 80%, 85%, 90%, and 95%, and any integer percentage and fraction thereof from 5% to 95%, depending on product function.

A saponified oil suitable for use with the presently disclosed compositions, formulations, and solutions can be prepared by hydrolysis of a vegetable oil, i.e., a triglyceride extracted from a plant, or an animal fat with a strong alkali, such as sodium hydroxide, potassium hydroxide, or combinations thereof, to form the carboxylate salt, e.g., a sodium or potassium salt, and glycerol (also referred to as glycerin, i.e., propane-1,2,3-triol ($C_3H_8O_3$)).

Representative saponified oils suitable for use with the presently disclosed compositions, formulations, and solutions can be prepared by the saponification of vegetable oils and animal fats known in the art including, but not limited to, almond oil, apricot kernel oil, avocado oil, babassu oil, beef tallow, borage oil, canola oil, castor oil, cocoa butter, coconut oil, corn oil, cottonseed oil, crisco shortening, emu oil, grapeseed oil, hazelnut oil, illipe butter, jojoba oil, kukui nut oil, lard, macadamia nut oil, mango butter, neem oil, olive oil, palm oil, palm kernel oil, peach kernel oil, peanut oil, rice bran oil, safflower oil, sesame oil, shea butter, soybean oil, stearic acid, sunflower oil, walnut oil, and wheat germ oil.

The saponified oils used in the presently disclosed methods generally are substantially free of glycerol. By "substantially free" is meant that the presently disclosed compositions, formulations, and solutions comprise, in some embodiments, less than about 1.0 percent by weight, in some embodiments, less than about 0.5 percent by weight, in some embodiments, less than 0.25 percent by weight, and in some embodiments, less than 0.1 percent by weight of the total composition. In other embodiments, however, glycerol can be added to the presently disclosed compositions, formulations, and solutions.

One of ordinary skill in the art would appreciate that the ingredients, such as the oil and the alkali, used in the saponification process can influence the characteristics of the presently disclosed cleaning/detergent composition, formulation, or solution. Such characteristics can include, but are not limited to, hardness or softness of the soap product, cleansing ability, fluffy lather, stable lather, stability in solution, and, in some embodiments, skin care qualities.

For example, coconut oil provides a stable solution with excellent cleaning ability and a fluffy, but unstable, lather, whereas palm oil also provides excellent cleaning ability, but, in contrast to coconut oil, provides a stable, but not fluffy, lather. Olive oil contains natural antioxidants and creates a creamy lather, whereas beef tallow forms a firm, white bar and creates a stable lather.

Further, potassium hydroxide can be used to prepare a soft soap or liquid soap due to its greater solubility, whereas sodium hydroxide can be used to prepare a bar soap. In some embodiments, any residual or excess alkali can be removed to decrease the harshness, irritability, and/or potential toxicity of the soap.

In some embodiments, the saponified oil is provided in an amount ranging from about zero point one percent (0.1%) by weight to about thirty three percent (33.0%) by weight, including 0.1%, 1%, 2.5%, 5%, 10%, 15%, 20%, 25%, 30%, and 33%, and any integer percentage and fraction thereof from about 0.1% to about 33%, depending on product function. In other embodiments, the saponified oil is provided in an amount ranging from about zero point one percent (0.1%) by weight to about 100% percent (100.0%) by weight, including 0.1%, 1%, 2.5%, 5%, 10%, 15%, 20%, 25%, 30%, 35%, 40%, 45%, 50%, 55%, 60%, 65%, 70%, 75%, 80%, 85%, 90%, 95%, 99%, and 100%, and any integer percentage and fraction thereof from about 0.1% to about 100%, depending on product function.

In some embodiments, the presently disclosed organic cleaning mixture comprises one or more of sodium carbonate, sodium hydroxide, and potassium hydroxide, wherein, in some embodiments, the one or more of sodium carbonate, sodium hydroxide, and potassium hydroxide is provided in an amount of about zero percent (0.0%) to about three percent (3.0%), including 0.5%, 1.0%, 1.5%, 2.0%, 2.5%, and 3.0%, and any integer percentage and fraction thereof from about 0.0% to about 3.0%, depending on product function. In other embodiments, the one or more of sodium carbonate, sodium hydroxide, and potassium hydroxide is provided in an amount of about zero percent (0.0%) to about thirty percent (30%), including 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10%, 15%, 20%, 25%, and 30%, and any integer percentage and fraction thereof from about 0.0% to about 30%, depending on product function.

In some embodiments, the viscosifier is provided in an amount ranging from about zero point five percent (0.5%) to about fifteen percent (15%), including 0.5%, 1.0%, 1.5%, 2.0%, 2.5%, 5%, 10%, and 15%, and any integer percentage and fraction thereof depending on product function. As used herein, the term "viscosifier" refers to any material that increases the viscosity of a fluid and also can be referred to as a "thickener" or "thickening agent." Representative viscosifiers include, but are not limited to, xanthan gum, guar gum, aragum, gum arabic, arrowroot powder, soy lecithin, or any cellulosic, such as methylcellulose or ethylcellulose, or starch based viscosifier.

When the presently disclosed solutions are mixed with water, the water, in some embodiments, comprises an amount ranging from about sixty three percent (63.0%) to about seventy eight percent (78.0%), including 63%, 64%, 65%, 66%, 67%, 68%, 69%, 70%, 71%, 72%, 73%, 74%, 75%, 76%, 77%, and 78% by weight, and any fraction thereof, of the total volume. In other embodiments, the water comprises an amount ranging from about fifty percent (50.0%) to about ninety percent (90.0%), including about 50%, 55%, 60%, 65%, 70%, 75%, 80%, 85%, and 90%, by weight, and any fraction thereof, of the total volume.

Further, depending on the particular formulations, additional soapberry extracts or derivatives thereof, glycerin, citric acid, aloe, salts, enzymes, and/or sodium derivatives can be provided in differing amounts as illustrated by the examples described herein below to provide appropriate texture, foaming capabilities, and foam stability. Representative enzymes include, but are not limited to, proteases, amylases, including bacilliary amylases, lipases, and cellulases. Representative sodium derivatives include, but are not limited to, sodium bicarbonate, sodium percarbonate, sodium borate, and trisodium phosphate.

In some embodiments, the presently disclosed organic cleaning mixtures also include one or more essential oils. Essential oils can be used for fragrancing, cleaning properties, preservation, soil penetration, saponification, and therapeutic benefits. Representative essential oil include, but are not limited to, allspice, ambrette seed, amyris, angelica root, anise, star anise, atlas cedarwood, Peru balsam, basil, holy basil, bay, bay laurel, beeswax absolute, benzoin absolute, bergamot, bergamot mint, black pepper, blue cypress, boisde-rose, boronia, bursera graveolens, cajeput, cananga, cardamom, carrot seed, cassia, catnip/catmint, atlas cedarwood, Virginian cedarwood, German chamomile, Roman chamomile, chocolate peppermint, cinnamon, citronella, clary sage, clove bud, coffee, common sage, coriander, cumin, cypress, blue cypress, davana, dill, dalmation sage, elemi, eucalyptus, lemon eucalyptus, radiata eucalyptus, fennel, fir needle, frankincense, galbanum, geranium, rose geranium, ginger, grapefruit, gurjum balsam, helichrysum, hyssop, immortelle, jamine absolute, juniper berry, kanuka, abrialis lavandula, lavender, lavendin, lemon, lemon balm, lemon eucalyptus, lemongrass, lemon myrtle, lime, linden blossom, mandarin, mandravasarotra, manuka, marjoram, may chang, melissa, mullein, myrrh, myrtle, lemon myrtle, neroli, niaouli, nutmeg, oakmoss, oliganum, bitter orange, sweet orange, oregano, palmarosa, palo santo, parsley, patchouli, peppermint, petitgrain, berry/leaf pimento, scotch pine, ravensara, rose, rosemary, rosewood, common sage, Spanish sage, sandalwood, saro, spearmint, spikenard, spruce, tagetes, tangerine, common tea tree, lemon tea tree, New Zealand tea tree, thyme, tobacco, tuberose, tulsi, vanilla, vetiver, violet leaf, yarrow, ylang ylang, and yuzu.

The presently disclosed organic cleaning mixtures also can include one or more of the following ingredients, including, but not limited to, salt, such as sea salt, kosher salt, Epsom salt, and standard table salt; viscosifiers, such as agar flakes, guar, modified guar, xanthan, sodium alginate, sodium alginate/calcium chloride, modified xanthan, gellan gum, carrageenan, soy lecithin, egg yoke, corn starch, and sodium chloride; natural surfactants, such as yucca, quillaja, yucca/quillaja natural blends, jojoba, and buffaloberry; oils for saponification, such as, coconut, glycerin, olive, jajoba, and palm; acids, such as acetic dry, standard grade acetic acid, i.e., "vinegar," (4% acidity or activity), acetic 120 (12% acidity or activity), acetic 300 (30% acidity or activity), any of which can be diluted to obtain an acetic acid percent acidity or activity having a range from about 0.001% to about 30%, including, but not limited to 0.001%, 0.01%, 0.1%, 1%, 5%, 10%, 15%, 20%, 25%, and 30%, and any integer percentage and fraction thereof from 65% to 95%, depending on product function, citric dry, citric liquid, malic, lactic, tartaric, formic, and phosphoric; and alcohols, such as ethyl and isopropyl alcohol.

Importantly, the presently disclosed compositions, formulations, and/or solution are "organic." As used herein, the term "organic" refers to a product or ingredient that complies with 7 CFR §205.301, which establishes organic content requirements for labeling and marketing purposes. Four categories of organic content have been established by the United States Department of Agriculture (USDA) under the National Organic Program (NOP): "100 percent organic," which is defined as products comprising 100 percent organic ingredients; "organic," which is defined as products comprising 95 percent or more organic ingredients; "made with organic," which is defined as products comprising between 70 percent to 95 percent organic ingredients; and "ingredient panel only," which is defined as products comprising less than 70 percent organic ingredients.

More particularly, under 7 CFR §205.301, all of the ingredients in products sold, labeled, or represented as "100 percent organic" must be certified organic and contain (by weight or fluid volume, excluding water and salt) 100 percent organically produced ingredients.

Products sold, labeled, or represented as "organic" must contain (by weight or fluid volume, excluding water and salt) not less than 95 percent organically produced raw or processed agricultural products. Any remaining product ingredients must be organically produced, unless not commercially available in organic form, or must be nonagricultural substances or non-organically produced agricultural products as specified on the National List under 7 CFR §205.605. Accordingly, non-organic ingredients allowed per National List may be used, up to a combined total of five percent of non-organic content (excluding salt and water).

Products sold, labeled, or represented as "made with organic" must contain (by weight or fluid volume, excluding water and salt) at least 70 percent organically produced ingredients. Accordingly, multi-ingredient agricultural products in the "made with organic" category must include at least 70 percent certified organic ingredients (excluding salt and water). Although any remaining agricultural products are not required to be organically produced, non-agricultural products must be specifically allowed on the National List under 7 CFR §205.605.

Multi-ingredient products having less than 70 percent certified organic content (excluding salt and water) are not qualified to be certified. Accordingly, any non-certified product must not include the USDA organic seal anywhere or the word "organic" on a principal display panel. Such products may only list certified organic ingredients as organic in the ingredient list and the percentage of organic ingredients. Remaining ingredients are not required to follow the USDA organic regulations.

Further, under 7 CFR §205.605, specified nonagricultural (nonorganic) substances may be used as ingredients in or on processed products labeled as "organic" or "made with organic," including the following nonsynthetic and synthetic ingredients:

Nonsynthetics: acids (alginic; citric—produced by microbial fermentation of carbohydrate substances; and lactic); agar-agar; animal enzymes—(rennet—animals derived; catalase—bovine liver; animal lipase; pancreatin; pepsin; and trypsin); bentonite; calcium carbonate; calcium chloride; calcium sulfate—mined; carrageenan; dairy cultures; diatomaceous earth—food filtering aid only; egg white lysozyme (CAS #9001-63-2); enzymes derived from edible, nontoxic plants, nonpathogenic fungi, or nonpathogenic bacteria; flavors, nonsynthetic sources only and must not be produced using synthetic solvents and carrier systems or any artificial preservative; gellan gum (CAS #71010-52-1)—high-acyl form only; glucono delta-lactone—production by the oxidation of D-glucose with bromine water is prohibited; kaolin; L-Malic acid (CAS #97-67-6); magnesium sulfate, nonsynthetic sources only; microorganisms—any food grade bacteria, fungi, and other microorganism; nitrogen—oil-free grades; oxygen—oil-free grades; perlite—for use only as a filter aid in food processing; potassium chloride; potassium iodide; sodium bicarbonate; sodium carbonate; tartaric acid—made from grape wine; waxes—nonsynthetic (Carnauba wax; and Wood resin); yeast—nonsynthetic, growth on petrochemical substrate and sulfite waste liquor is prohibited (autolysate; bakers; brewers; nutritional; and smoked—nonsynthetic smoke flavoring process must be documented); and synthetics: activated charcoal (CAS #s 7440-44-0; 64365-11-3)—only from vegetative sources; for use only as a filtering aid; alginates; ammonium bicarbonate—for use only as a leavening agent; ammonium carbonate—for use only as a leavening agent; ascorbic acid; calcium citrate; calcium hydroxide; calcium phosphates (monobasic, dibasic, and tribasic); carbon dioxide; cellulose—for use in regenerative casings, as an anti-caking agent (non-chlorine bleached) and filtering aid; chlorine materials—disinfecting and sanitizing food contact surfaces, except that residual chlorine levels in the water shall not exceed the maximum residual disinfectant limit under the Safe Drinking Water Act (calcium hypochlorite; chlorine dioxide; and sodium hypochlorite); cyclohexylamine (CAS #108-91-8)—for use only as a boiler water additive for packaging sterilization; diethylaminoethanol (CAS #100-37-8)—for use only as a boiler water additive for packaging sterilization; ethylene—allowed for postharvest ripening of tropical fruit and degreening of citrus; ferrous sulfate—for iron enrichment or fortification of foods when required by regulation or recommended (independent organization); glycerides (mono and di)—for use only in drum drying of food; glycerin—produced by hydrolysis of fats and oils; hydrogen peroxide; lecithin—bleached; magnesium carbonate—for use only in agricultural products labeled "made with organic" prohibited in agricultural products labeled "organic"; magnesium chloride—derived from sea water; magnesium stearate—for use only in agricultural products labeled "made with organic" prohibited in agricultural products labeled "organic"; nutrient vitamins and minerals, in accordance with 21 CFR 104; 20, Nutritional Quality Guidelines For Foods; octadecylamine (CAS #124-30-1)—for use only as a boiler water additive for packaging sterilization; ozone; pectin (low-methoxy); peracetic acid/peroxyacetic acid (CAS #79-21-0)—for use in wash and/or rinse water according to FDA limitations; for use as a sanitizer on food contact surfaces; phosphoric acid—cleaning of food-contact surfaces and equipment only; potassium acid tartrate; potassium carbonate; potassium citrate; potassium hydroxide—prohibited for use in lye peeling of fruits and vegetables except when used for peeling peaches during the Individually Quick Frozen (IQF) production process; potassium iodide—for use only in agricultural products labeled "made with organic," prohibited in agricultural products labeled "organic"; potassium phosphate—for use only in agricultural products labeled "made with organic," prohibited in agricultural products labeled "organic"; silicon dioxide; sodium acid pyrophosphate (CAS #7758-16-9)—for use only as a leavening agent; sodium citrate; sodium hydroxide—prohibited for use in lye peeling of fruits and vegetables; sodium phosphates—for use only in dairy foods; sulfur dioxide—for use only in wine labeled "made with organic grapes," provided that total sulfite concentration does not exceed 100 ppm; tartaric acid—made from malic acid; tetrasodium pyrophosphate (CAS #7722-88-5)—for use only in meat analog products; tocopherols—derived from vegetable oil when rosemary extracts are not a suitable alternative; and xanthan gum.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The descriptions and specific examples that follow are only intended for the purposes of illustration, and are not to be construed as limiting in any manner to make compounds of the disclosure by other methods.

Example 1

Representative Procedure for Preparing Formulations for Laundry Detergent, Hard Surface Cleaner, Hand Soap, Automatic Dishwasher Detergent, Human Shampoo, and Animal Shampoo The procedure described is for a five hundred (500) gallon batch. Weights are based on a specific gravity for water of eight point thirty-four (8.34) pounds per gallon. As will be apparent to those of ordinary skill in the art, adjustments can be made depending on variation in the batch size.

Initially, a blending vessel is filled with two hundred and fifty (250) gallons of blend water. Stirring or circulation is initiated depending on the vessel design. Thereafter, approximately 69 gallons (575 pounds/about 13.8 wt. %) of soapberry extract is added to the blend vessel. Stirring is continued until a uniform solution is achieved. This normally takes about two (2) to three (3) minutes.

After the solution is uniform, about thirty four gallons (290 pounds/about 7.0 wt. %) of forty one percent solids (41%) saponified oil is added to the blend vessel. Stirring is continued for an additional five (5) minutes.

Thereafter, 10 pounds (0.2 wt. %) of glycerin is added to the vessel. Stirring continues for five (5) minutes.

Thereafter, in a separate vessel, 10 pounds (0.2 wt. %) of a viscosifier, such as, but not limited to xanthan, is hydrated in 250 gallons of water.

After hydration of the viscosifier is complete, the solution is added to the base solution and stirring continued for an additional 30 minutes.

Additional blend water is added to a total weight of four thousand one hundred seventy (4,170) pounds for a five hundred (500) gallon batch. Stirring is continued for fifteen (15) minutes and thereafter the batch is complete.

In preparing the solution, the solution should be a white to a light yellow with no separation or settling. The pH of the solution should be about nine point five (9.5) point to about ten point five (10.5), including 9.5, 9.6, 9.7, 9.8, 9.9, 10.0, 10.1, 10.2, 10.3, 10.4, and 10.5, depending on water quality. After completion of the first batch, the pH is measured and set as the target specification, allowing for plus or minus point three (0.3). Two (2) quarts of the completed solution is kept as a quality control sample.

In preparing a hand cleaner formulation, a similar procedure is based on a five hundred (500) gallon batch and weights are based on a specific gravity for water of eight point thirty-four (8.34) pounds per gallon as before A blending vessel is filled with two hundred and fifty (147) gallons of blend water. Stirring or circulation is initiated depending on the vessel design. Thereafter, approximately 69 gallons (575 pounds/about 13.8 wt. %) of soapberry extract is added to the blend vessel. Stirring is continued until a uniform solution is achieved. Uniformity typically is achieved in about two (2) to three (3) minutes.

After the solution is uniform, about thirty four gallons (290 pounds/about 7.0 wt. %) of forty one percent solids (41%) saponified oil is added to the blend vessel. Stirring is continued for an additional five (5) minutes.

Thereafter, 10 pounds (0.2 wt. %) of glycerin is added to the vessel. Stirring continues for five (5) minutes.

Thereafter, in a separate vessel, 10 pounds (0.2 wt. %) of a viscosifier, such as, but not limited to xanthan, is hydrated in 250 gallons of water.

After hydration of the viscosifier is complete, the solution is added to the base solution and stirring continued for an additional 30 minutes.

Thereafter additional blend water is added to a total weight of four thousand one hundred seventy (4,170) pounds for a five hundred (500) gallon batch. Stirring is continued for fifteen (15) minutes and thereafter the batch is complete.

In preparing the solution, the solution should be a white to a light yellow with no separation or settling. The pH of the solution should be about nine point five (9.5) point to about ten point five (10.5), including 9.5, 9.6, 9.7, 9.8, 9.9, 10.0, 10.1, 10.2, 10.3, 10.4, and 10.5, depending on water quality. After completion of the first batch, the pH is measured and set as the target specification, allowing for plus or minus point three (0.3). Two (2) quarts of the completed solution is kept as a quality control sample.

Example 2

Organic Laundry Detergent

An organic laundry detergent includes active components constituting ninety five percent (95.0%) organic materials by weight, and includes sixty four percent (64.0%) by weight soapberry extract, thirty two percent (32.0%) by weight saponified oil, one percent (1.0%) glycerin by weight, one percent (1.0%) xanthan by weight, one percent (1.0%) by weight sodium carbonate and up to one percent (1.0%) by weight enzymes. The previously listed components are mixed into water at a ratio of twenty one hundredths (0.21) of a pound of total components to one (1.0) pound of water.

Example 3

Organic Hard Surface Cleaner

An organic hard surface cleaner includes active components constituting ninety five percent (95.0%) organic materials by weight, and includes sixty five percent (65.0%) by weight soapberry extract, thirty three percent (33.0%) by weight saponified oil, one percent (1.0%) glycerin by weight and one percent (1.0%) xanthan by weight. The previously listed components are mixed into water at a ratio of twenty one hundredths (0.21) of a pound of total components to one (1.0) pound of water.

Example 4

Organic Hand Soap

An organic hand soap includes active components constituting ninety five percent (95.0%) organic materials by weight, and includes sixty five percent (65.0%) by weight soapberry extract, thirty three percent (33.0%) by weight saponified oil, one percent (1.0%) glycerin by weight and one percent (1.0%) xanthan by weight. The previously listed components are mixed into water at a ratio of twenty one hundredths (0.21) of a pound of total components to one (1.0) pound of water.

Example 5

Organic Automatic Dishwashing Detergent

An organic automatic dishwashing detergent includes active components constituting ninety five percent (95.0%) organic materials by weight, and includes eighty two percent (82.0%) by weight soapberry extract, twelve percent (12.0%) by weight saponified oil, one point five percent (1.5%) by weight sodium carbonate, two point eight percent (2.8%) by weight citric acid and one percent (1.0%) by weight xanthan. This composition also can include point seven percent (0.7%) by weight silicate. The previously-listed components are mixed into water at a ratio of thirty seven hundredths (0.37) of a pound of total solution to one (1.0) pound of water.

Example 6

Organic Human Shampoo

An organic shampoo includes active components constituting ninety five percent (95.0%) organic materials by weight, and includes sixty five percent (65.0%) by weight soapberry extract, thirty three percent (33.0%) by weight saponified oil, one percent (1.0%) glycerin by weight and one percent (1.0%) xanthan by weight. The previously listed components are mixed into water at a ratio of twenty one hundredths (0.21) of a pound of total components to one (1.0) pound of water.

Example 7

Organic Animal Shampoo

An organic animal shampoo includes active components constituting ninety five percent (95.0%) organic materials by weight, and includes sixty five percent (65.0%) by weight soapberry extract, thirty three percent (33.0%) by weight saponified oil, one percent (1.0%) glycerin by weight and one percent (1.0%) xanthan by weight. The previously listed components are mixed into water at a ratio of twenty one hundredths (0.21) of a pound of total components to one (1.0) pound of water.

Example 8

Automatic Dish Detergent

In this example, an automatic dish detergent can be prepared comprising between about 70% to about 75% by weight soapberries extract, between about 10% to about 15% by weight saponified oils, between about 0.1% to about 5% by weight sodium carbonate, between about 5% to about 15% by weight guar gum, between about 0.5% to about 2.5% by weight sodium hydroxide, between about 0.5% to about 2.5% by weight lemongrass, and less than 1% by weight ethyl palmate, silica, and organic white thyme oil, not including salt and water.

Example 9

Laundry Detergent

In this example, a laundry detergent can be prepared comprising between about 70% to about 85% by weight, soapberries extract, between about 10% to about 20% by weight saponified oils, between about 0.5% to about 2% by weight guar gum, between about 0.5% to about 5% by weight of a first enzyme, e.g., Medley Core, and about 0.5% to about 2.0% by weight of a second enzyme, e.g., Celluclean® 5000L, and less than 1% hydrogen peroxide, sodium carbonate, calcium chloride, white thyme, organic lavender, not including salt and water.

Example 10

Laundry Detergent

In this example, a laundry detergent can be prepared comprising between about 90% to about 100% by weight saponified oils, between about 0.1% to about 5% by weight sodium carbonate, between about 0.5% to about 10% by weight guar gum, between about 0.5% and 5% white thyme, and less than 1% soap bark, and organic lavender, not including salt and water.

Example 11

Free and Clear Laundry Detergent

In this example, a free and clear laundry detergent can be prepared comprising between about 70% to about 80% by weight soapberries extract, between about 15% to about 25% by weight saponified oils, between about 0.5% and about 1.5% xanthan gum, between about 0.5% and 1.5% by weight a first enzyme, e.g., Celluclean® 5000L, and less than 1% aragum, a second enzyme, e.g., Medley Core, sodium carbonate, calcium chloride, and thyme oil essential oil, not including salt and water.

Example 12

Laundry Detergent

In this example, a laundry detergent can be prepared comprising between about 20% to about 30% by weight soapberries extract, between about 70% to about 80% by weight saponified oils, between about 0.5% to about 2% by weight aragum, between about 0.5% and about 5% xanthan gum, between about 0.5% and about 2.0% sodium carbonate, and less than 1% soap bark and organic lavender, not including salt and water.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. An organic cleaning mixture comprising from about five percent (5%) to about ninety five percent (95%) by weight soapberry extract, from about 0.1% to about 95% percent (95%) by weight saponified oil, and from about 0.5% to about thirty percent (30%) by weight of one or more of sodium carbonate, sodium hydroxide, potassium hydroxide, an alkali, and combinations thereof, not including water, wherein the mixture comprises at least one of (i) not less than 95 percent organically produced raw or processed agricultural products, or (ii) at least 70 percent certified organic ingredients, excluding salt and water.

2. The mixture of claim 1, wherein the mixture comprises from about twenty percent (20%) to about eighty-five percent (85%) by weight soapberry extract, from about 0.1% to about eighty percent (80%) by weight saponified oil, and optionally from about 0.5% to about thirty percent (30%) by weight of one or more of sodium carbonate, sodium hydroxide, and potassium hydroxide, not including water.

3. The mixture of claim 2, wherein the mixture comprises from about sixty-five percent (65%) to about eighty-five percent (85%) by weight soapberry extract, from about ten percent (10%) to about twenty-five percent (25%) by weight saponified oil, from about 1% to about 15% of a thickener, and optionally from about 0.5% to about three percent (3%) by weight of one or more of sodium carbonate, sodium hydroxide, and potassium hydroxide, not including water.

4. The mixture of claim 3, wherein the mixture further comprises one or more components selected from the group consisting of hydrogen peroxide, ethyl palmate, sodium hydroxide, calcium chloride, one or more enzymes, silica, and one or more fragrances.

5. The mixture of claim 2, wherein the mixture comprises from about fifteen percent (15%) to about twenty-five percent (25%) by weight soapberry extract, from about seventy percent (70%) to about eighty percent (80%) by weight saponified oil, from about 1% to about 15% of a thickener, and optionally from about 0.5% to about thirty percent (30%) by weight of one or more of sodium carbonate, sodium hydroxide, and potassium hydroxide, not including water.

6. The organic cleaning mixture of claim 1, wherein the mixture comprises from about seventy percent (70%) to about eighty-five percent (85%) by weight soapberry extract, from about ten percent (10%) to about twenty-five percent (25%) by weight saponified oil, from about 0.1% to about five percent (5%) by weight of sodium carbonate, and from about 0.5% to about fifteen percent (15%) by weight of a viscosifier, not including water.

7. The organic cleaning mixture of claim 6, further comprising one or more components selected form the group consisting of glycerin, one or more enzymes, citric acid, silica, one or more sodium derivatives, sodium hydroxide, soap bark, calcium chloride, ethyl palmate, lemon grass, thyme oil, hydrogen peroxide, organic lavender, and combinations thereof.

8. The organic cleaning mixture of claim 6, wherein the mixture comprises from about seventy (70%) to about seventy-five percent (75%) by weight soapberry extract, between about ten percent (10%) to about fifteen percent (15%) by weight saponified oils, between about 0.1% to about 5% by weight sodium carbonate, between about 5% to about 15% guar gum, between about 0.5% to about 2.5% sodium hydroxide, between about 0.5% and about 2.5% lemongrass, and less than about 1% by weight each of ethyl palmate, silica, and thyme oil.

9. The organic cleaning mixture of claim 6, wherein the mixture comprises from about seventy (70%) to about eighty-five percent (85%) by weight soapberry extract, between about ten percent (10%) to about twenty (20%) by weight saponified oils, less than about 0.1% by weight sodium carbonate, between about 0.5% to about 2% by weight guar gum, between about 0.5% to about 5.0% by weight of a first enzyme, between about 0.5% to about 2.0% by weight of a second enzyme, and less than about 1% by weight each of thyme oil, hydrogen peroxide, calcium chloride, and organic lavender.

10. The organic cleaning mixture of claim 6, wherein the mixture comprises from about seventy (70%) to about eighty percent (80%) by weight soapberry extract, between about fifteen percent (15%) to about twenty-five (25%) by weight saponified oils, less than about 0.1% by weight sodium carbonate, between about 0.5% to about 1.5% by weight xanthan gum, between about 0.5% to about 1.5% by weight of a first enzyme, less than about 1% by weight of a second enzyme, and less than about 1% by weight each of thyme oil, calcium chloride, aragum, soap bark, and organic lavender.

11. A detergent comprising the organic cleaning mixture of claim 6.

12. The detergent of claim 11, wherein the detergent is selected from the group consisting of a laundry detergent and an automatic dishwasher detergent.

13. The organic cleaning mixture of claim 1, wherein the mixture comprises from about twenty percent (20%) to about thirty percent (30%) by weight soapberry extract, from about seventy percent (70%) to about 80 percent (80%) by weight saponified oil, from about 0.5% to about two percent (2%) by weight of sodium carbonate, and from about 0.5% to about five percent (5%) by weight of a first viscosifier and about between 0.5% and about two percent (2.0%) by weight of a second viscosifier, not including water, wherein the mixture comprises at least one of (i) not less than 95 percent organically produced raw or processed agricultural products, or (ii) at least 70 percent certified organic ingredients, excluding salt and water.

14. The organic cleaning mixture of claim 13, further comprising one or more fragrances and soap bark.

15. A laundry detergent comprising the organic cleaning mixture of claim 13.

16. An organic cleaning mixture, comprising from about ninety percent (90%) to about 100 percent (100%) by weight saponified oil, from about 0.1% to about five percent (5%) by weight of sodium carbonate, and from about 0.5% to about ten percent (10%) by weight of a viscosifier, not including water, wherein the mixture comprises at least one of (i) not less than 95 percent organically produced raw or processed agricultural products, or (ii) at least 70 percent certified organic ingredients, excluding salt and water.

17. The organic cleaning mixture of claim 16, further comprising between about 0.5% and about 5% by weight thyme oil.

18. A laundry detergent comprising the organic cleaning mixture of claim 16.

19. The organic cleaning mixture of claim 1, wherein the mixture comprises from about five percent (5%) to about fifteen percent (15%) by weight soapberry extract, from about eighty-five percent (85%) to about ninety-five percent (95%) by weight saponified oil, from about 0.5% to about 1.5% by weight of sodium carbonate, from about 0.0% to about 1.0% sodium hydroxide, from about 2.5% to about percent (5%) by weight of a viscosifier, and further comprising ethyl alcohol and less than about 1% soap bark, not including water.

20. The organic cleaning mixture of claim 1, wherein the mixture comprises from about twenty-five percent (25%) to about thirty-five percent (35%) by weight soapberry extract, from about fifty-five percent (55%) to about seventy-five percent (75%) by weight saponified oil, from about 0.5% to about 1.5% by weight of sodium carbonate, from about 0.0% to about 1.0% sodium hydroxide, from about 2.5% to about percent (5%) by weight of a viscosifier, and further comprising ethyl alcohol and less than about 1% soap bark, not including water.

\* \* \* \* \*